United States Patent [19]

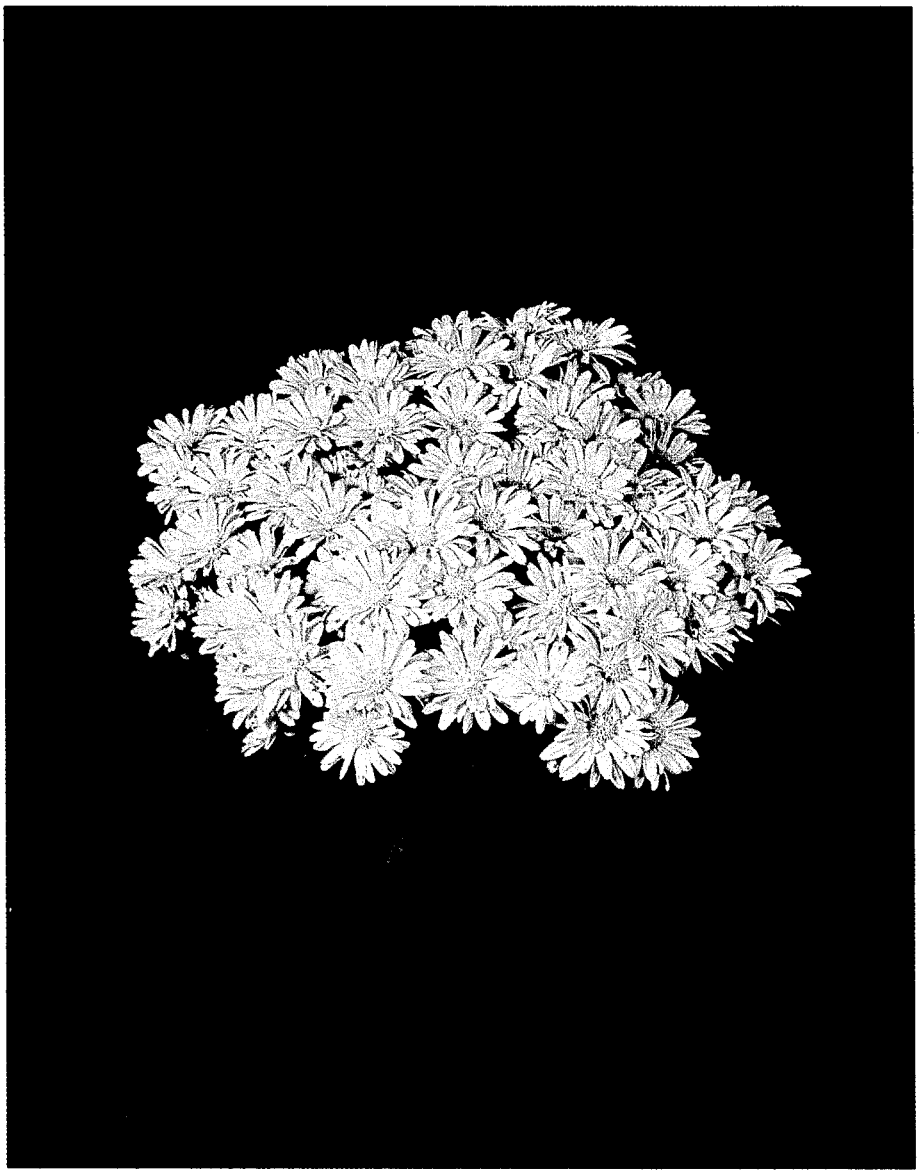
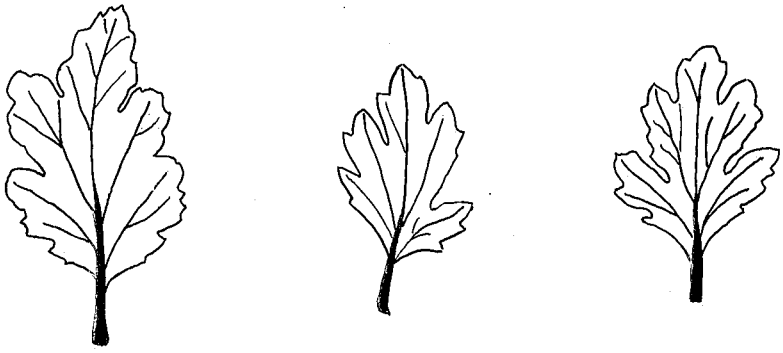

Shoesmith

[11] Plant 4,120

[45] Oct. 4, 1977

[54] CHRYSANTHEMUM PLANT NAMED PINK CONCORD

[75] Inventor: Leonard H. Shoesmith, Westfield-Woking, England

[73] Assignee: Pan-American Plant Company, West Chicago, Ill.

[21] Appl. No.: 733,472

[22] Filed: Oct. 15, 1976

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Rummler and Snow

[57] ABSTRACT

A new and distinct cultivar of pot chrysanthemum plant characterized by its single flower form and flowers which have several rows of pink ray florets which possess good substance and long life and which have a minimal production of pollen. This new variety is not temperature sensitive, has an upright pot habit and good breaking ability, and an abundant production of flowers when grown as a spray plant.

1 Drawing Figure

BACKGROUND OF THE NEW PLANT

My new variety of chrysanthemum plant originated as a seedling of unidentified parentage and was discovered by me in 1972, at Westfield-Woking, Surrey, England, among a group of random pollinated plants cultivated by me in the course of a breeding program carried on by me with the object of developing new chrysanthemum varieties suitable for production for the commercial market. This new plant was asexually reproduced by me at Westfield-Woking, Surrey, England, in 1972, by cuttings from the original plant, and then tested for its retention of its originally noted distinctive characteristics. Since 1972, asexual propagation of this new variety has been carried on at West Chicago, Ill., and at Cortez, Fla., by means of vegetative cuttings, and many generations of the plant so propagated have demonstrated that its novel and distinctive characteristics hold true from generation to generation and appear to be firmly and permanently fixed.

DESCRIPTION OF THE DRAWING

This new variety of chrysanthemum plant is illustrated by the accompanying photographic drawing which shows a potted plant display of the flowers in full color as nearly true as is reasonably possible to obtain by conventional photographic procedures, and which shows, by pen-and-ink drawings, the distinctive configuration of the leaves of the new plant taken at several stages of maturity.

DESCRIPTION OF THE NEW PLANT

The following is a detailed description of my new variety of chrysanthemum plant as observed of greenhouse plants grown at West Chicago, Ill., in 1975 and 1976, the color designations being according to the R.S.H. Colour Chart published by The Royal Horticultural Society of London, England.

THE PLANT

Origin: Seedling.

Parentage: Unidentified, discovered among random pollinated greenhouse plants.

Classification:

*Botanic.*—*Chrysanthemum morifolium.*

*Commerical.*—Greenhouse pot plant.

Form: Perennial herbaceous bush.

Height: 10 to 12 inches.

Growth: Terminal. Upright and vigorous, sturdy and with good strength.

Branching: Normal, under natural conditions.

Foliage: Abundant in quantity — 6 to 8 leaves per 4 inches of stem.

*Size of leaf.*—2½ to 3½ inches long and 1⅛ to 1⅞ inches wide for the mature leaf.

*Shape of leaf.*—Lobed and slightly serrated.

*Surface texture.*—Canescent.

*Venation.*—Pinnately veined.

*Color.*—Upper side — Green 137A. Under side — Yellow-Green 146A.

*Petioles.*—½ to ⅝ inch long.

THE BUD

Form: Almost global.

Size: ⅜ to 7/16 inch in diameter. ¼ inch in depth.

Opening: Slowly.

Color:

*When phyllaries first divide.*—Yellow-Green 144A.

*When florets begin to unfurl.*—Orange 29C to Orange Red 31D.

Phyllaries: Many upstanding and spear-shaped bracts borne on the outside of the receptacle.

*Color.*—Inside — Green 137C. Outside — Green 137C.

*Surface texture.*—Pubescent.

Peduncle: Length — 1½ to 3 inches.

*Strength.*—Erect.

*Surface texture.*—Pubescent.

THE FLOWER

Response: 9 week. This plant can be flowered the year around with photoperiod control.

Natural flowering season: October 20 to 27.

Recommended flowering: Year around.

Blooms:

*Flower type.*—Single and composite.

*Borne.*—A head of many florets on a receptacle.

*Shape.*—When bloom first opens — flat.

*Size.*—Diameter — 2 to 2½ inches. Depth — ⅝ to ⅞ inch.

*Florets.*—Number — numerous. Form: Linear.

| Color: | January | May | August |
|---|---|---|---|
| Outer floret: | Red-Purple 73B | Red-Purple 73C | Purple 75C |
| Reverse side: | Red-Purple 73D | Red-Purple 73D | Red-Purple 69A |

Firmness: Medium. Appearance: Very slight shine. Discoloration: Slight fade as bloom becomes aged.

*Peduncle.*—1½ to 3 inches long. Sturdy and upright. Color: Green 137C.

Persistence: Blooms hang on and dry.

Lasting quality: On plant — 3 weeks. Not recommended as cut flower.

REPRODUCTIVE ORGANS

Stamens: Number — 5 syngenesious.

*Arrangement.*—Connate by their anthers to form a cylinder about the style.

*Filaments.*—Length — 1/16 to ⅛ inch. Color: Light Yellow.

*Pollen.*—Color — Yellow.

Pistils: Number — One to each ray and disc floret.

*Style.*—3/16 to ¼ inch long.

*Stigmas.*—Color — Yellow.

Ovaries: Inferior and bicarpellate.

* * * * *

UNITED STATES PATENT OFFICE

CERTIFICATE OF CORRECTION

Patent No. Plant 4120 Dated October 4, 1977

Inventor(s) Leonard H. Shoesmith

It is certified that error appears in the above-identified patent and that said Letters Patent are hereby corrected as shown below:

Add the following text and claim to the specification:

This new chrysanthemum plant is particularly distinguished by its single flower form and its pink ray florets, of which there are several rows, which possess good substance and long life with a minimal production of pollen. This variety is also characterized by its small foliage, strong stems, and good breaking ability, with 4 to 6 breaks when manually pinched, and by its abundant production of flowers when grown as a spray pot.

This variety is not temperature sensitive and can be flowered the year around on medium treatment, flowering nine weeks after commencement of short days and requiring but one 2500 ppm B-9 application during the optimum growing periods.

UNITED STATES PATENT OFFICE

CERTIFICATE OF CORRECTION

Patent No. Plant 4120 Dated October 4, 1977

Inventor(s) Leonard H. Shoesmith

It is certified that error appears in the above-identified patent and that said Letters Patent are hereby corrected as shown below:

I claim:

1. A new and distinct cultivar of chrysanthemum substantially as herein shown and described, characterized by its single flower form with several rows of pink ray florets and minimal pollen production, its upright pot habit and good breaking ability, and its abundant production of flowers when grown as a spray pot plant.

Signed and Sealed this

*Fifteenth* Day of *May 1979*

[SEAL]

*Attest:*

RUTH C. MASON
*Attesting Officer*

DONALD W. BANNER
*Commissioner of Patents and Trademarks*